United States Patent
Wong et al.

(10) Patent No.: US 6,595,951 B1
(45) Date of Patent: Jul. 22, 2003

(54) CLOSURE SYSTEM FOR AN ACTIVE AGENT DELIVERT DEVICE

(75) Inventors: Patrick S. -L. Wong, Burlingame, CA (US); James Horvath, San Jose, CA (US); Radomir N. M. Vukadin, Cupertino, CA (US); Joyce C. Anthony, Woodside, CA (US); Vincent J. Ferrari, Foster City, CA (US); Jeffrey W. Etter, Hayward, CA (US); Christopher M. G. Ohms, Redwood City, CA (US)

(73) Assignee: Alza Corporation, Palo Alto, CA (US)

( * ) Notice: Subject to any disclaimer, the term of this patent is extended or adjusted under 35 U.S.C. 154(b) by 0 days.

(21) Appl. No.: 09/575,074

(22) Filed: May 19, 2000

Related U.S. Application Data

(62) Division of application No. 08/950,016, filed on Oct. 14, 1997, now Pat. No. 6,096,003.
(60) Provisional application No. 60/028,703, filed on Oct. 18, 1996.

(51) Int. Cl.[7] ............................................. A61M 37/00
(52) U.S. Cl. .......................................... 604/85; 604/83
(58) Field of Search .............................. 604/77, 78, 81, 604/83, 85, 133, 185, 89, 247, 257

(56) References Cited

U.S. PATENT DOCUMENTS

| | | | |
|---|---|---|---|
| 2,436,505 A | 2/1948 | DuRall | |
| 2,867,536 A | 1/1959 | Mead et al. | |
| 3,610,483 A | 10/1971 | Visconti et al. | |
| 3,845,770 A | 11/1974 | Theeuwes et al. | |
| 3,995,631 A | 12/1976 | Higuchi et al. | 604/83 |
| 4,034,756 A | 7/1977 | Higuchi et al. | 604/83 |
| 4,111,202 A | 9/1978 | Theeuwes | 604/83 |
| 4,320,759 A | 3/1982 | Theeuwes | 604/83 |
| 4,327,725 A | 5/1982 | Cortese et al. | 604/83 |
| 4,449,983 A | 5/1984 | Cortese et al. | 604/83 |
| 4,581,013 A | 4/1986 | Allen | 604/83 |
| 4,765,989 A | 8/1988 | Wong et al. | 604/83 |
| 4,792,333 A | 12/1988 | Kidder | 604/83 |
| 4,981,468 A * | 1/1991 | Benefiel et al. | 604/83 |
| 5,094,861 A | 3/1992 | D'Auguste et al. | 604/83 |
| 5,110,597 A | 5/1992 | Wong et al. | |
| 5,123,915 A | 6/1992 | Miller et al. | |
| 5,222,940 A | 6/1993 | Wilk | |
| 5,223,259 A | 6/1993 | Lackney | |
| 5,330,426 A | 7/1994 | Kriesel et al. | |
| 5,387,421 A | 2/1995 | Amidon et al. | |
| 5,391,381 A | 2/1995 | Wong et al. | |
| 5,603,695 A | 2/1997 | Erickson | |
| 5,718,681 A | 2/1998 | Manning | |
| 5,780,058 A | 7/1998 | Wong et al. | |
| 5,910,321 A | 6/1999 | Wong et al. | |

OTHER PUBLICATIONS

Kikendall, M.D. et al., Digestive Diseases and Sciences, vol. 28, No. 2 (Feb. 1983), "Pill–Induced Esophageal Injury".
Derwent Abstract, Wk. 9637, B07, 96–363246/37, DE 19503104–A1, Tomasek, J., 95.02.01, 95 DE–1003104.

* cited by examiner

*Primary Examiner*—Manuel Mendez
(74) *Attorney, Agent, or Firm*—Andrea G. Reister; Covington & Burling

(57) ABSTRACT

The present invention is directed to a closure system for an oral active agent delivery device. The device comprises an elongate tubular member having first and second ends. The closure system includes a deformable closure means adapted to allow delivery of the active agent upon deformation. The closure system prevents spillage and maintains the integrity of the dose within the device. In use, the closure system is deformed and separated from the second end of the tubular member, liquid is drawn up into the first end of the member, and the liquid and active agent are drawn out of the second end of the member and into the patient's mouth.

2 Claims, 5 Drawing Sheets

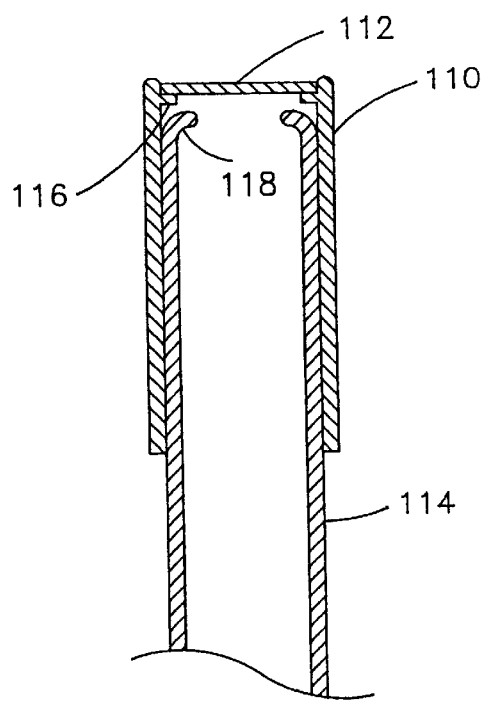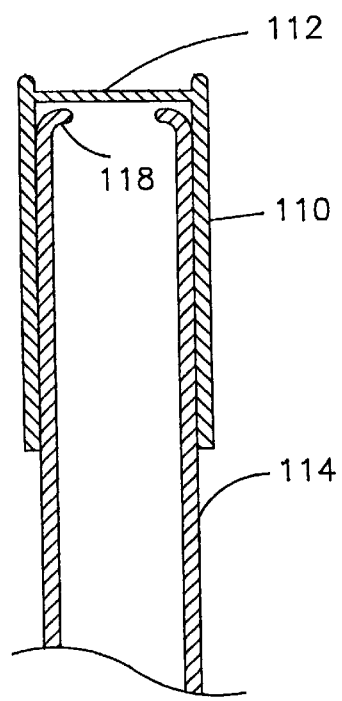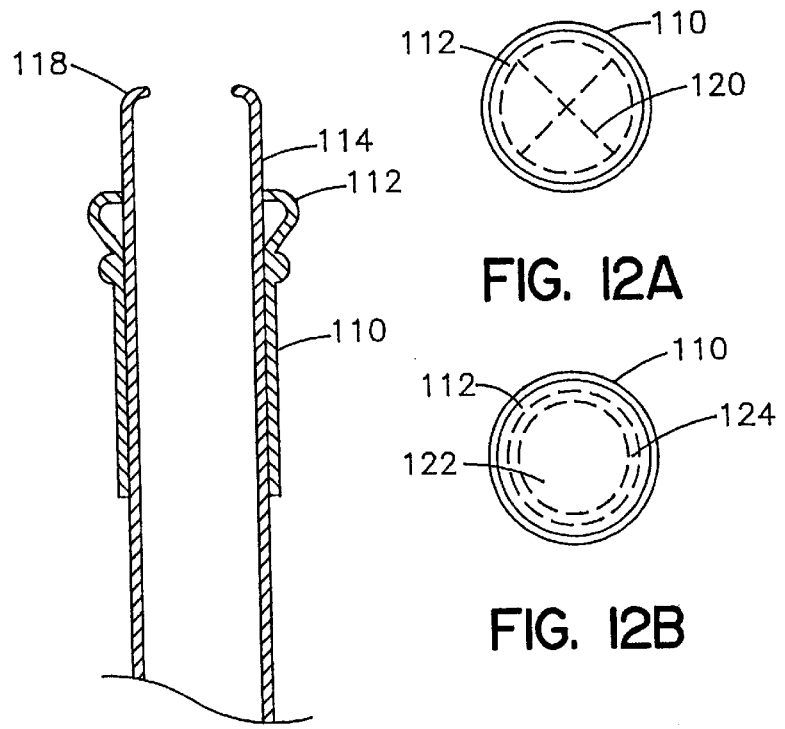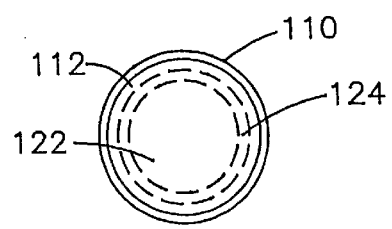
FIG. 11A
FIG. 11B
FIG. 12A
FIG. 12B
FIG. 13

CLOSURE SYSTEM FOR AN ACTIVE AGENT DELIVERT DEVICE

This application is a divisional of application Ser. No. 08/950,016, filed Oct. 14, 1997, now U.S. Pat. No. 6,096, 003, which claims the benefit of U.S. Provisional Application No. 60/028,703 filed Oct. 18, 1996.

FIELD OF THE INVENTION

The present invention is related to the oral delivery of an active agent. More particularly, it is a closure system for an active agent delivery device. The active agent delivery device comprises a lumen containing an active agent in the form of discrete units through which a fluid is drawn when suction is applied to one end of the device.

BACKGROUND OF THE INVENTION

Tablets, capsules, caplets and many other types of devices have been used for oral delivery of active agents. These forms are relatively easy to manufacture and convenient for use in the hospital or other institutional settings or at home. Many different types of active agents have been incorporated into such dosage forms—ranging from analgesics to antibiotics to hormones.

There are patients that, because of age or infirmity, have difficulty swallowing solid oral dosage forms. According to Kikendall et al., *Digestive Diseases and Sciences* 28:2 (1983), there were 221 cases documented between 1970–1982 of tablet and capsule induced esophageal injury. The most commonly implicated drugs were tetracycline (108 cases), emepronium bromide (36 cases), potassium chloride (16 cases) and ferrous salts (12 cases).

In view of the above, various approaches have been proposed whereby swallowing of a large solid system is avoided as is described in the following patents and applications which are all incorporated by reference herein.

U.S. Pat. No. 2,436,505 to DuRall describes a pill douser for administering medicines in liquid form or in pills or tablets. The device has a bowl at the top for containing the medicine and a tube that can be submerged in a liquid held in a drinking glass. The liquid is drawn upward for administering the liquid and any pill or tablet present in the bowl.

U.S. Pat. No. 2,867,536 to Mead et al. describes an improved drinking straw where a soluble flavoring material is contained within an annular space contained within an inner and an outer tube. The inner tube has a bore through which liquid can be drawn. During use, the upper and lower caps are removed, the flavoring material is emptied into the liquid and the flavored liquid is drawn up through the inner tube and into the mouth.

U.S. Pat. No. 3,610,483 to Visconti describes a dispensing device for liquid medication that is formed in the shape of a straw. A predetermined dose of liquid medication is loaded into the straw which is then capped at both ends until the medication is dispensed when a patient removes the caps and sucks air into the device.

U.S. Pat. No. 4,581,013 to Allen is directed to a doser for orally administering a medication. A tube with a removable closure and a radially extending plate supports a solid medication and permits passage of a stream of liquid. The tube is fitted on top of a straw that is placed into a liquid.

U.S. Pat. No. 4,792,333 to Kidder describes a tamper proof package for containing and orally administering a solid substance. A tube has two portions that are separated by a supporting and confining means that supports and confines the solid substance but permits fluid flow. The ends of the tube are hermetically sealed.

U.S. Pat. No. 4,981,468 to Benefiel et al. is directed to a unit dosage form for delivering a therapeutic agent in free-flowing form. A slanted grid supports the dose between two ends of a tube.

PCT patent application Ser. No. PCT/US96/11812 describes an oral active agent delivery system comprising a hollow chamber that contains discrete units of active agent. A fluid passing retainer prevents release of the discrete units but permits fluid entry into the chamber. The retainer is transportable with the fluid entering the system.

A variety of other oral delivery systems have been described. These include a medicated pacifier (U.S. Pat. No. 5,123,915 to Miller et al.) and a lollipop type device for delivery of a solid medicament (U.S. Pat. No. 5,223,259 to Lackney). None of these devices or the devices described previously provide for the delivery of a solid medicament into the oral cavity as a bolus dose, while avoiding the difficulties inherent in swallowing a solid system such as a tablet or a capsule or the shelf-life problems encountered when a medicine is dissolved or dispersed in a fluid, where the integrity of the dose of active agent is maintained and where inadvertent swallowing of the device, or portions thereof, is avoided. Furthermore, there is a need for simple, easy to use, and reliable closure systems for active agent delivery systems.

SUMMARY OF THE INVENTION

Accordingly, in one aspect the present invention is directed to a closure system for preventing spillage from an active agent delivery device. The device comprises a first tubular member with a first end suitable for placement in a liquid and a second end suitable for placement in the mouth of a patient and contains an active agent in the form of discrete units. The closure system comprises a deformable closure means that upon deformation is adapted to open the first end of the tubular member and allow transport of active agent therethrough. The deformation of the closure means preferably is irreversible so as to serve as an indication of prior use or misuse of the delivery device.

In another aspect, the closure system comprises a second tubular member that concentrically surrounds the second end of said first tubular member. A protuberance on the first end of the second tubular member extends towards the first end of the first tubular member. The second end of the second tubular member is closed to prevent spillage of the active agent.

In still another aspect, the invention is a closure system for preventing spillage from an active agent delivery device where the closure system comprises a second tubular member that has an inner portion and an outer portion. The inner portion extends inside the second end of the first tubular member of the delivery device and comprises a cutting edge and the outer portion comprises a rupturable membrane.

In yet another aspect, the invention is a closure system for preventing spillage from an active agent delivery device, where a tubular member has a first end and a second end. The second end is closed and further is in part removable in order to permit a patient to suck up the active agent from the second end of the device after the first end has been inserted into a fluid.

In a further aspect, the invention is a closure system for preventing spillage from an active agent delivery device, where a tubular member has a first end and a second end. The second end comprises a valve that is normally closed and is openable in order to permit a patient to suck up the active agent from the second end of the device after the first end has been inserted into a fluid.

In still another aspect, the invention is a method for preventing loss of an active agent from an active agent delivery device. The method comprises providing a tubular member with a first end and a closed second end, opening the second end in order to expose the active agent and placing the second end in the mouth to deliver the agent by sucking. The portions of the device that remain following delivery are too large to be swallowed by the patient.

DESCRIPTION OF THE DRAWINGS

The figures are not drawn to scale, but are set forth to illustrate various embodiments of the invention. Like numbers refer to like structures.

FIGS. 11A and 11B are side, cross-sectional views of another embodiment of the closure system of the invention.

FIGS. 12A and 12B are top views of preferred forms of the embodiment of the closure system of FIGS. 11A and 11B.

FIG. 13 is a side, cross-sectional view of the device of FIGS. 11A and 11B after opening of the closure system.

DETAILED DESCRIPTION OF THE INVENTION

The present invention provides closure systems for oral active agent delivery devices. The active agent is in the form of discrete units and is contained within the lumen of an active agent delivery device. The closure systems prevent spillage of the agent from the device, allow for convenient and accurate delivery of a measured dose of active agent to a patient and provide an indication of prior use or misuse of the device.

Definitions

The term "discrete units" intends the active agent in solid or particulate form.

The term "oral dosage form" means that the active agent is placed in a discrete unit that is delivered orally and is capable of maintaining its physical configuration and chemical integrity while housed within the delivery device.

The term "therapeutically effective amount" means the amount of the active agent needed to effect the desired pharmacologic, often beneficial, result.

The term "fluid passing active agent retainer" means a valve, plug, grid, restriction or the like that allows for passage of fluid but does not allow for passage of other ingredients such as the active agent that is contained in the delivery device.

The term "deformable" means capable of being either wholly or partially altered in shape or form.

The dispensing devices of the invention find use where it is inconvenient or unsafe to use oral dosage forms such as capsules or tablets. The devices may be particularly useful in geriatric or pediatric patient populations, but they may also be useful for those who have difficulty swallowing capsules or tablets. A single delivery device or several devices can be administered to a patient during a therapeutic program.

The closure system of the present invention comprises a deformable closure means that is adapted upon deformation to open an end of the delivery device for access by a patient and allow transport of the active agent therethrough. Deformation of the closure means preferably is irreversible and provides an indication of prior use or misuse of the delivery device. Such an indication is beneficial since the dose of active agent to be delivered typically is in the form of discrete units, such as granules or powder, and the correct quantity of active agent to be delivered cannot often be determined by visual observation alone. Accordingly, should the delivery device be opened and partially used (i.e., not all of the dose dispensed) or some of the active agent removed, the deformable closure means will provide an indication of such use. Particularly when the deformation is irreversible, observation of the deformation is easily made and appropriate procedures to prevent any deleterious effects from any prior use or misuse can be undertaken. As an added benefit, the closure system of the present invention facilitates efficiency and economy in manufacture and use of the systems. Various embodiments of the closure system comprising a deformable closure means are described below.

Figures 1, 2:
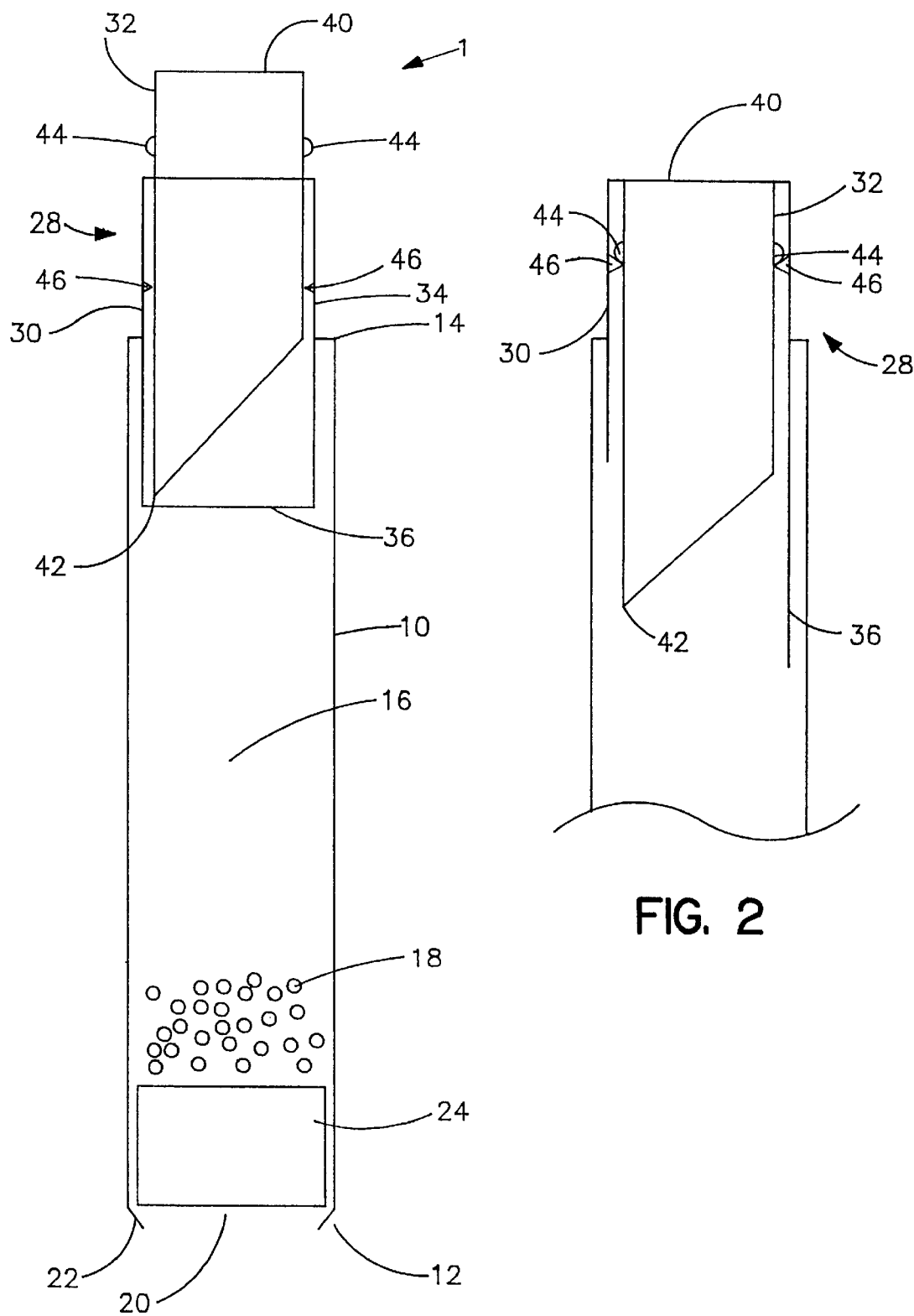
FIG. 1 is a side view of one embodiment of an active agent delivery device with a closure system containing a membrane according to the invention.
FIG. 2 is a side view of the device closure system of FIG. 1 following rupture of the membrane.
Figure 3:
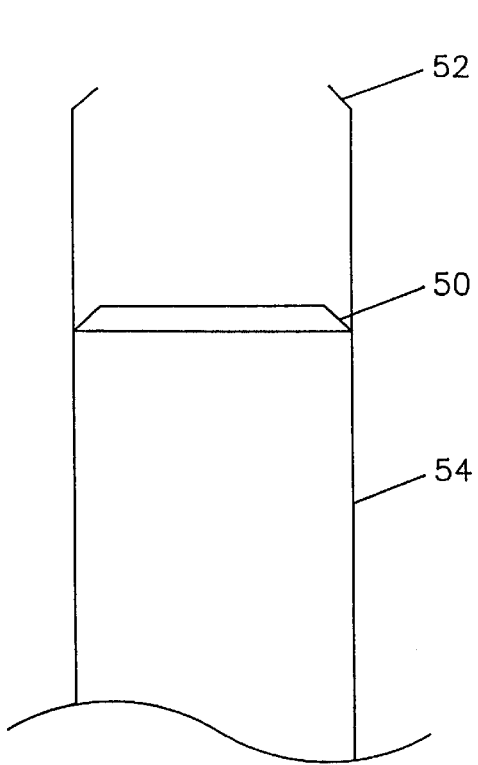
FIG. 3 is a side view of a second embodiment of the device closure system of the invention.
Figure 4:
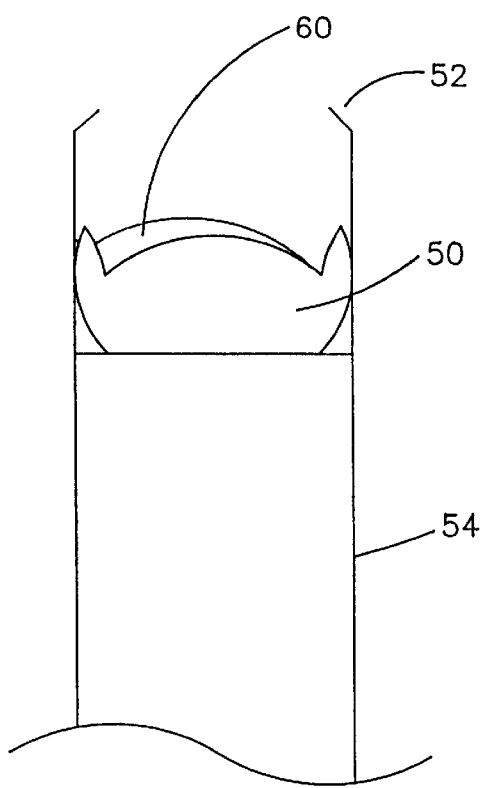
FIG. 4 is a side view of the closure system of FIG. 3 following opening of the closure system.
Figure 5:
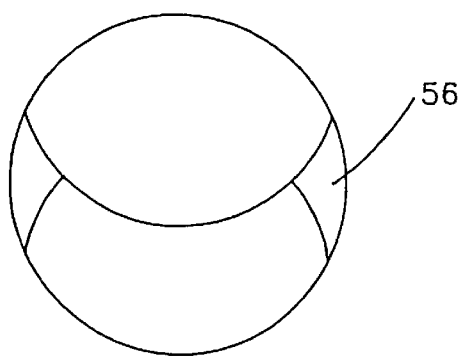
FIG. 5 is a top view of the device closure system of FIGS. 3 and 4.

FIG. 1 depicts, in a side view, one embodiment of the delivery device according to the invention. The device is in prepared form prior to placement in a fluid. Dispensing device 1 is shown in FIG. 1 to comprise an elongate tubular member 10 with a first end 12 and a second end 14. Contained within tubular member 10 is a lumen 16 that contains an active agent 18 and a fluid passing active agent retainer 20. The fluid passing active agent retainer 20 comprises a restriction 22 and a plug 24. The restriction 22 is formed by crimping the end of tubular member 10. The inner diameter of the restriction 22 is smaller than the outside diameter of the plug 24 such that the active agent 18 and plug 24 are retained within the tubular member 10 but plug 24 can slide upwardly in lumen 16 as fluid is drawn therethrough.

FIG. 1 further shows a closure system for the delivery device. A second tubular member 30 comprises an inner portion 32 and an outer portion 34. The outer portion 34 fits inside the second end of the first tubular member and has a frangible membrane 36 that seals the lumen 16 of the first tubular member 10. The inner portion 32 comprises a lumen and has a blunt end 40 and a cutting edge 42. The inner portion 32 further has two or more detents 44. When in use, the blunt end 40 of the inner portion 32 of the second tubular member 30 is depressed. The cutting edge 42 pierces the membrane 36. Resistance to further depression will occur when the detents 44 reach corresponding detents 46 of the second tubular member 30. FIG. 2 shows the second end 14 of the first tubular member and the closure system 28 after depression of the inner portion 32 of the second tubular member 30 and the rupture of membrane 36. Following rupture of membrane 36, the first end 12 of the device 1 is then placed in a fluid and the second end 14 is placed in the mouth of a patient. The patient begins to suck and fluid is drawn up through lumen 16. The discrete units are entrained in the fluid drawn through lumen 16 and easily swallowed. Rupture of membrane 36 results in membrane 36 being irreversibly deformed and provides an indication of use of the device.

Figure 6:
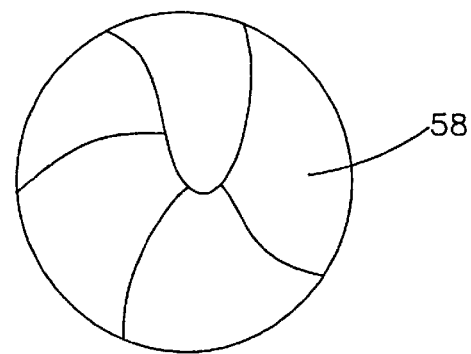
FIG. 6 is an alternative top view of the closure system of FIGS. 3 and 4.

FIGS. 3, 4, 5 and 6 show a second embodiment of a device closure system according to the invention. In this embodiment, the closure system comprises a valve 50 near the second end 52 of the first tubular member 54. Alternative valve designs are shown as an overleaf valve 56 (FIG. 5) and an aperture valve 58 (FIG. 6). When in use, the second end 52 of the first tubular member 54 is placed into the mouth of a patient and by virtue of the sucking and fluid pressure exerted, the valve 50 will open and the dose will be delivered through the opening 60 created in the valve 56 (see FIG. 4). Suction and flow of liquid through the valve result in its deformation.

Figure 7:
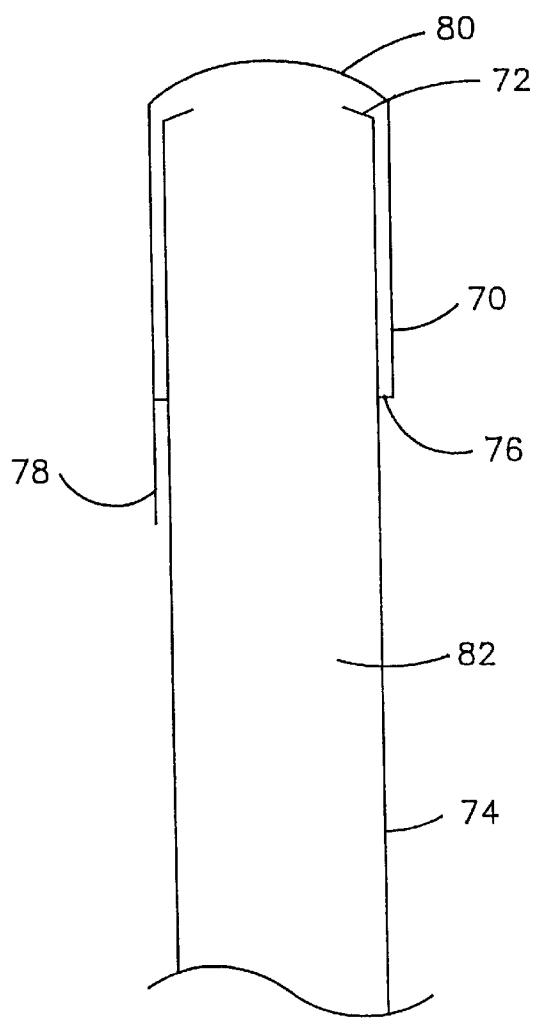
FIGS. 7, 8, 9 and 10 are side views of other embodiments of the device closure system according to the invention.
Figure 8:
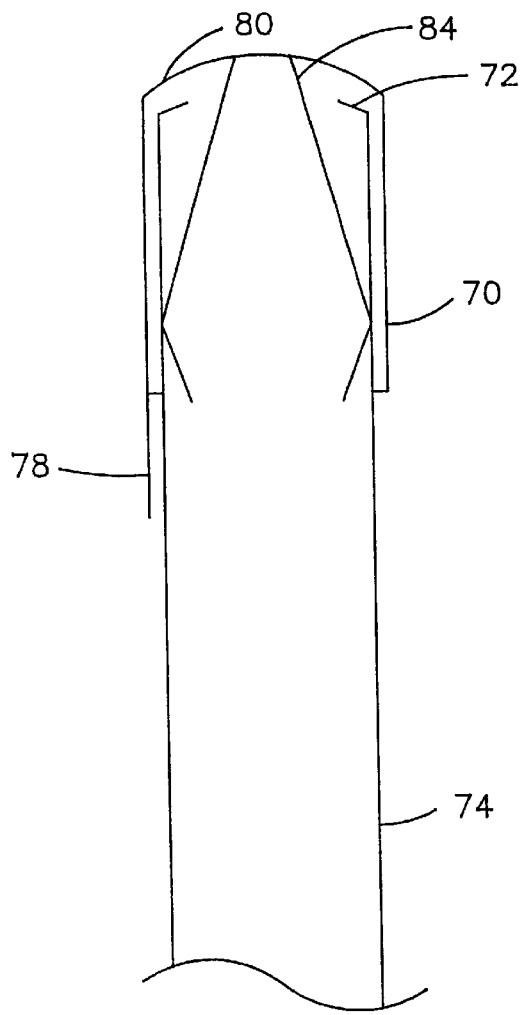

FIGS. 7 and 8 show further embodiments of the device closure system of the invention. In these embodiments, a second tubular member 70 is placed over the second end 72 of the first tubular member 74. The second tubular member 70 has a first end 76 that contains a protuberance 78 for easy handling of the member 70. The second end 80 is closed to seal the lumen 82 of the first tubular member 74. The second tubular member is long enough (between 2 and 12 cm preferably between about 3 and 8 cm) to prevent inadvertent swallowing of the member 70. In the embodiment shown in FIG. 8, a flexible member 84 inside the first tubular member aids in retaining the second tubular member 70 on the first tubular member 74. Although the flexible member 84 is shown to be a two-prong member, it may comprise a solid or cylindrical plug or other configuration that can hold the member 70 in place. In use, the patient or care giver will grab the protuberance 78, lift the second tubular member 70 off of the first tubular member 74 and insert the second end 72 of the first tubular member 74 into the mouth of the patient to suck for delivery of the dose of active agent entrained in a liquid drawn through the first end of the first tubular member 74. Generally, the force applied to protuberance 78 and second tubular member 70 during removal will result in deformation to the protuberance 78 and to second tubular member 70 as well.

Figure 9:
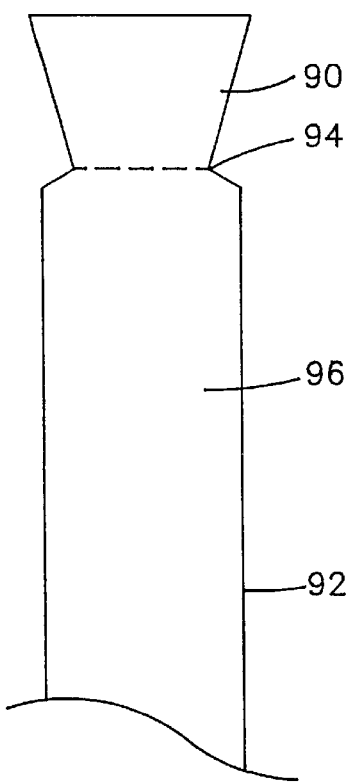

FIG. 9 shows another embodiment of a closure system of the invention. In this embodiment, the second end 90 of the first tubular member 92 itself comprises the closure system. A perforation 94 in the member 92 allows for cutting or tearing of the member 92, exposure of the active agent containing lumen 96 and delivery of the active agent by sucking. Again, the portion 90 of the member 92 that is removed is between 2 and 8 cm, preferably about 3 and 6 cm such that it is too large to be inadvertently swallowed.

Figure 10:
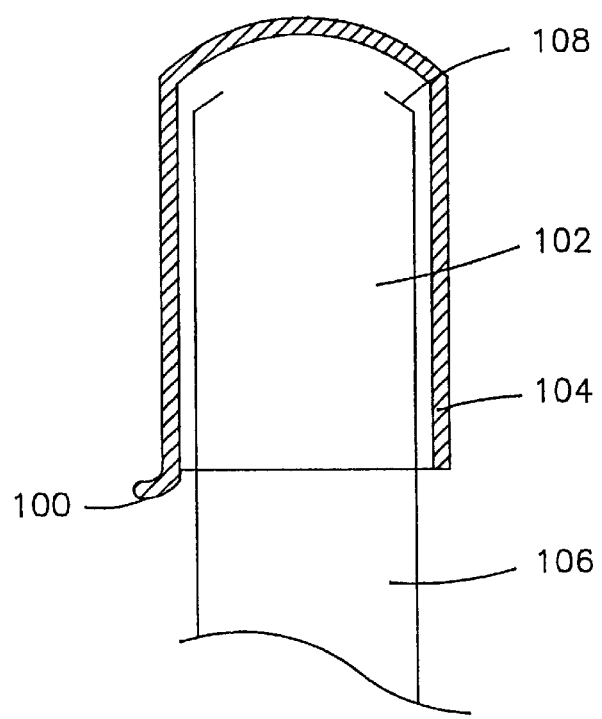

FIG. 10 shows a further embodiment of the closure system of the invention. In this embodiment, a tab 100 on the second tubular member 102 can be pulled to remove a strip 104 of the member 102 extending the length of the member 102 over the top of the member 102 and down its other side. In this way, the member 102 will be divided into two pieces and fall away from the first tubular member 106. The second end 108 of the first tubular member 106 can then be placed into the mouth of the patient. Again, the remaining pieces of the second tubular member 102 are large enough to prevent inadvertent swallowing. Removal of strip 104 results in the irreversible deformation of the member 102.

FIGS. 11–13 show further embodiments of the closure system of the invention. In this embodiment a second tubular member 110 comprising a frangible membrane 112 extends over first tubular member 114. As shown in FIG. 11A, frangible membrane 112 can for formed separately from second tubular member 110 and heat sealed, welded, glued or otherwise sealed to a projection 116 formed on the internal surface of second tubular member 110 near its top end. Optionally, the seal can be formed such that it will release the membrane from the second tubular member 110 when second tubular member 110 is moved downwardly toward the bottom end of first tubular member 114. The membrane itself may not rupture but the effect is equivalent. Such a configuration is contemplated within the term "frangible membrane" as used herein. In those configurations wherein the seal releases, the thickness of the membrane may be chosen more for manufacturing efficiency and economy without regard to considerations relating to the rupture of the membrane itself. Alternatively, as illustrated in FIG. 11B, frangible membrane 112 may be integrally formed with second tubular member 110 such as by injection molding. In each case, frangible membrane 112 has a thickness that permits the membrane to be broken and irreversibly deformed when second tubular member 110 is pushed downwardly along first tubular member 114.

The upper end 118 of first tubular member 114 will contact and break membrane 112 as second tubular member 110 is pushed toward the bottom end of first tubular member 114, as illustrated in FIG. 13. To facilitate breaking of membrane 112, membrane 112 can be formed with one or more weakened portions, illustrated by score lines 120 in FIG. 12A. Preferably membrane 112 is formed with a thicker center portion 122 and a thinner annular ring 124 near the outside edge of membrane 112, as shown in FIG. 12B, to promote tearing and rupture of membrane 112 upon movement of second tubular member 110 toward the bottom end of first tubular member 114. When first tubular member 114 breaks membrane 112, membrane 112 will open about the outer circumference of first tubular member 114 and move downwardly with second tubular member 110 out of the way of the upper end 118, thereby providing unencumbered access to the upper end 118 for placement into the mouth of the patient. Since the second tubular member 110 and frangible membrane 112 are retained on first tubular member 114, swallowing of the remainder of the second tubular member 110 and frangible membrane 112 by a patient is prevented.

The active agent itself may be in liquid, solid, or semisolid form and formulated into discrete units. The agents may be soluble and insoluble charged or uncharged molecules, components of molecular complexes or nonirritating, pharmacologically acceptable salts and may contain additional material such as binders, coating materials, or stabilizers such that the active agent is formed into one or more discrete units. The discrete units may be designed in a multitude of ways to provide a specific drug delivery profile. One embodiment comprises an active agent that is in particulate form. These particulates are generally between about 50 and 2000 $\mu$m in diameter, usually between about 100–500 $\mu$m in diameter. Where the particulate has an unpleasant taste, the particulate may be taste masked by methods that are well known in the art. The particulates may be designed to provide immediate delivery of the active agent, they may be coated to provide for prolonged release or delayed pulse release of the active agent, or they may be designed to provide for a combination of immediate, pulsed and/or prolonged delivery of active agent. The particulates may be coated with an enteric coating to provide for targeted release of the active agent.

In other embodiments, the active agent may be in liquid form and may be contained within a soft gelatin capsule or within a solid oral dosage form. These dosage forms may include, matrix or other types of tablets, pellets and elongated tablets where the height to diameter ratio exceeds one, capsules, microcapsules, elementary osmotic pumps, such as those described in U.S. Pat. No. 3,845,770, mini osmotic pumps such as those described in U.S. Pat. Nos. 3,995,631, 4,034,756, and 4,111,202, and multichamber osmotic systems referred to as push-pull and push-melt osmotic pumps, such as those described in U.S. Pat. Nos. 4,320,759, 4,327,725, 4,449,983, and 4,765,989 all of which are incorporated herein by reference.

The term "active agent" refers to an agent, drug, compound, composition of matter or mixture thereof which provides some pharmacologic, often beneficial, effect. This includes foods, food supplements, nutrients, drugs, vitamins, and other beneficial agents. As used herein, the terms further include any physiologically or pharmacologically active substance that produces a localized or systemic effect in a patient. The active drug that can be delivered includes antibiotics, antiviral agents, anepileptics, analgesics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of active agents useful in this invention include prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17b-estradiol, ethinyl estradiol, ethinyl estradiol 3-methyl ether, prednisolone, 17-b-hydroxyprogesterone acetate, 19-nor-progesterone, norgestrel, norethindrone, norethisterone, norethiederone, progesterone, norgesterone, norethynodrel, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captopril, mandol, guanabenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tertatolol, minoxidil, chlordiazepoxide, diazepam, amitriptyline, tetracycline, metronidazole, acyclovir, zidovudine and imipramine. Further examples are proteins and peptides which include, but are not limited to, insulin, coichicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin and luteinizing hormone.

It is to be understood that more than one active agent may be delivered in a device of this invention, and that the use of the term "agent" in no way excludes the use of two or more such agents. Combination products such as those described, for example, in U.S. Pat. No. 5,256,684 for the treatment of ulcers (tetracycline, metronidazole and bismuth subsalicylate) and for the treatment of AIDS (zidovudine (AZT), a protease inhibitor and 3TC) are particularly suited for delivery using the present invention.

The amount of active agent employed in the delivery device will be that amount necessary to deliver a therapeutically effective amount of the agent to achieve the desired result. In practice, this will vary widely depending upon the particular agent, the severity of the condition, and the desired therapeutic effect. However, the device is generally useful for active agents that must be delivered in fairly large doses of from about 100 mg to 5000 mg, usually in the range of from about 250 mg to about 2500 mg. However, since the devices may also be useful in pediatric patients, doses in the ranges of 25 to 250 mg are also contemplated herein.

Representative materials for forming devices including the active agent formulation chamber, the elongated tubular member and the closure systems, include, without limitation, paper, plastic such as propylene/styrene copolymers, polypropylene, high density polyethylene, low density polyethylene, ethylene vinyl acetate copolymer and the like. The devices usually have an outer diameter of between about 5 and 15 mm. The lumen has a diameter that is usually between about 4 and 14 mm and often between about 5 and 12 mm. The devices are between about 10 and 30 cm in length. Preferred materials for forming the membrane when it is integrally formed with the second tubular member are polypropylene and polymers from that polyolefin family. The thickness of the membrane typically is on the order of 0.075–0.25 mm. In those configurations where the membrane is sealed to the second tubular member, the membrane can be formed from frangible materials such as metallic foils, e.g., aluminum, aluminized plastic, uncoated and coated papers, e.g., waxed paper, and the like. The thickness of the materials will be chosen so that the force created when the second tubular member is forced downwardly over the top end of the first tubular member ruptures the membrane. Thicker membranes may be used in those instances when the membranes are provided with weakened portions, such as by scoring. In those cases, where the membrane is applied to the second tubular member with a releasable seal, the thickness of the membrane can be greater such that rupture of the membrane is effectively accomplished by forced release of the seal The fluid passing active agent retainer permits the free flow of fluid but prohibits passage of the active agent from the device prior to delivery. Where the retainer comprises a one-way plug or valve, the plug or valve will seal the tubular member containing active agent at atmospheric pressure. When suction is applied, fluid will be drawn through the one-way plug or valve into the lumen of the device. The plug can be configured to ascend to the top of the lumen as the active agent is delivered into the oral cavity. Preferably, the plug will have a bulk density of less than one. The suction end of the tubular member is adapted, e.g. by crimping, to prevent the plug from exiting the lumen. When suction is no longer applied, the plug will remain in the highest position it reached during sipping. Other forms of one way plugs can be a balloon of elastomeric material, a one-way mechanical ball valve and the like.

The drinkable fluid that is used for suspending the active agent formulation by sipping through the active agent formulation chamber is preferably any good-tasting liquid including but not limited to water, juice, milk, soda, coffee, tea etc. Care must be taken to ensure compatibility of the fluid with the active agent formulation.

The above description has been given for ease of understanding only. No unnecessary limitations should be understood therefrom, as modifications will be obvious to those skilled in the art.

What is claimed is:

1. A tubular device, comprising:

a tubular member having a first end suitable for placement in a liquid and a second end suitable for placement in the mouth of a patient;

discrete units comprising an active agent disposed in said tubular member, wherein said second end comprises a removable portion, thereby allowing the patient to suck the discrete units and the liquid through the device, wherein said removable portion is defined by a perforation; and a fluid passing active agent retainer disposed in said tubular member, wherein said fluid passing active agent retainer is configured to slide upwardly toward said second end of said tubular member as liquid is drawn therethrough.

2. The tubular device of claim 1, wherein said removable portion is from about 2 to about 8 cm in length.

* * * * *